United States Patent [19]

Welner

[11] Patent Number: 5,612,870
[45] Date of Patent: Mar. 18, 1997

[54] SYSTEM FOR TRACKING SECURE MEDICAL TEST CARDS

[75] Inventor: Stephen Welner, Martinsville, N.J.

[73] Assignee: Ortho Pharmaceutical Corporation, Raritan, N.J.

[21] Appl. No.: 366,785

[22] Filed: Dec. 30, 1994

[51] Int. Cl.$^6$ .................................................. G06F 15/00
[52] U.S. Cl. ............................................ 395/203; 283/900
[58] Field of Search ........................... 364/401 M, 401 R; 235/375, 380, 382; 340/825.31, 825.34; 283/900

[56] References Cited

U.S. PATENT DOCUMENTS

| | | | |
|---|---|---|---|
| 4,777,964 | 10/1988 | Briggs et al. | 128/760 |
| 4,815,768 | 3/1989 | Applebaum et al. | 283/67 |
| 4,979,515 | 12/1990 | Briggs et al. | 128/760 |
| 5,190,049 | 3/1993 | Briggs et al. | 128/760 |
| 5,325,294 | 6/1994 | Keene | 364/401 M |
| 5,509,064 | 4/1996 | Welner et al. | 379/265 |

*Primary Examiner*—Gail O. Hayes
*Assistant Examiner*—Steven R. Yount
*Attorney, Agent, or Firm*—Paul A. Coletti

[57] ABSTRACT

A method and apparatus are provided for tracking information associated with a plurality of test cards. Each of the test cards is anonymously associated with a patient such that the patient's identity is unknown to a central monitoring system. A first set of unique personal identification numbers (PINs) is stored in a PIN database in the central monitoring system, and a first digital signal representing PINs from the first set of unique PINs is provided to a test kit assembler. A second digital signal, representing test kits actually assembled, is received from the test kit assembler in the central monitoring system. Each of the test kits actually assembled includes a test card having one of the unique PINs from the first set of unique PINs associated therewith. The first set of unique PINs is tracked by updating the PIN database in response to the second digital signal. A third digital signal, representing a second set of unique PINs, is provided from the central monitoring system to a test lab in response to the second digital signal. A fourth digital signal, representing test cards received at the test lab from patients, is received from the test lab in the central monitoring system. The test cards are known to the central monitoring system only by the first set of unique PINs. The first set of unique PINs is further tracked from the central monitoring system by updating the PIN database and a test results database in response to the fourth digital signal.

16 Claims, 4 Drawing Sheets

5,612,870

SYSTEM FOR TRACKING SECURE MEDICAL TEST CARDS

BACKGROUND OF THE INVENTION

The present invention relates generally to systems for tracking objects moving amongst a plurality of locations. More particularly, the present invention is directed to a system for tracking medical test cards as such test cards move from their point of manufacture to a test lab for analysis. Still more particularly, the present invention relates to a system for tracking medical test cards for use with a confidential in-home test kit to be used by a consumer to test for the presence of the HIV virus (human immunodeficiency virus) which is known to cause AIDS (Acquired Immune Deficiency Syndrome).

AIDS is viewed by many as the single most serious modern-day health issue affecting society. Since there is presently no known cure for the disease, early detection and treatment of the HIV virus provides the best chance of helping a patient to prolong his or her life by delaying onset of the disease. In addition, early detection is crucial to preventing the spread of the virus itself.

Although early detection of the virus is vitally important, only about 8% of adult Americans are tested annually. Individuals have been reluctant to submit to testing because, among other things, they fear that a positive test result will not be kept confidential. It is currently estimated that the number of at-risk individuals being tested for the HIV virus would increase to approximately 29% if a diagnostic procedure was available the could assure an individual's confidentiality.

The present invention relates to a confidential at-home test system for determining whether an individual may be carrying the HIV virus. An individual uses the at-home system by purchasing a test kit at a pharmacy or other retail outlet. The test kit contains a test card for carrying a sample of the individual's blood to a testing lab. The individual places several drops of his or her blood onto the test card while at home, and then mails the test card to a central laboratory for testing. Several days later, the individual then calls a central phone number to get his or her testing results.

As mentioned above, it is vital that any HIV testing system have mechanisms for maintaining the anonymity of the individuals being tested. In addition, in order to maintain the integrity of a testing system such as the one described above, which may potentially involve the processing and handling of numerous test cards by a testing lab, it is crucial that the system also have mechanisms for continuously tracking the location and status of each test card in the system.

It is therefore an object of the present invention to provide a system for simultaneously tracking location and status information for a plurality of medical test cards as such test cards move amongst various locations.

It is a further object of the present invention to provide a medical test card tracking system which facilitates the collection and transmission of test status and result information to the individuals being tested while, at the same time, maintaining the anonymity of such individuals.

It is a still further object of the present invention to provide a medical test card tracking system which can identify counterfeit or unauthorized test cards submitted for analysis.

These and still other objects of the invention will become apparent upon study of the accompanying drawings and description of the invention.

SUMMARY OF THE INVENTION

The present invention is directed to a method and apparatus for tracking with a central monitoring system status and result information associated with a plurality of test cards. Each of the test cards in the system is anonymously associated with a patient such that the patient's identity is unknown to the central monitoring system. A first set of unique personal identification numbers (PINs) is stored in a personal identification number database in the central monitoring system, and a first digital signal representative of PINs from the first set of unique PINs is provided to a test kit assembler. A second digital signal is received in the central monitoring system from the test kit assembler. The second digital signal is representative of test kits actually assembled by the test kit assembler. Each of the test kits actually assembled includes a test card having one of the unique PINs from the first set of unique PINs associated therewith. At this point, the first set of unique PINs is tracked by updating the personal identification number database in response to the second digital signal. Next, a third digital signal is provided from the central monitoring system to a test lab. The third digital signal is representative of a second set of unique PINs and is provided by the central monitoring system in response to the second digital signal. A fourth digital signal is received in the central monitoring system from the test lab. The fourth digital signal is representative of test cards received at the test lab from patients. Each of the test cards received at the test lab is known to the central monitoring system only by one of the unique PINs from the first set of unique PINs, and the identities of patients associated with the test cards received at the test lab are anonymous to the central monitoring system. After the fourth digital signal is received, the first set of unique PINs is again tracked from the central monitoring system by updating the personal identification number database and a test results database in response to the fourth digital signal.

DETAILED DESCRIPTION OF THE PREFERRED EMBODIMENT

Figure 1:
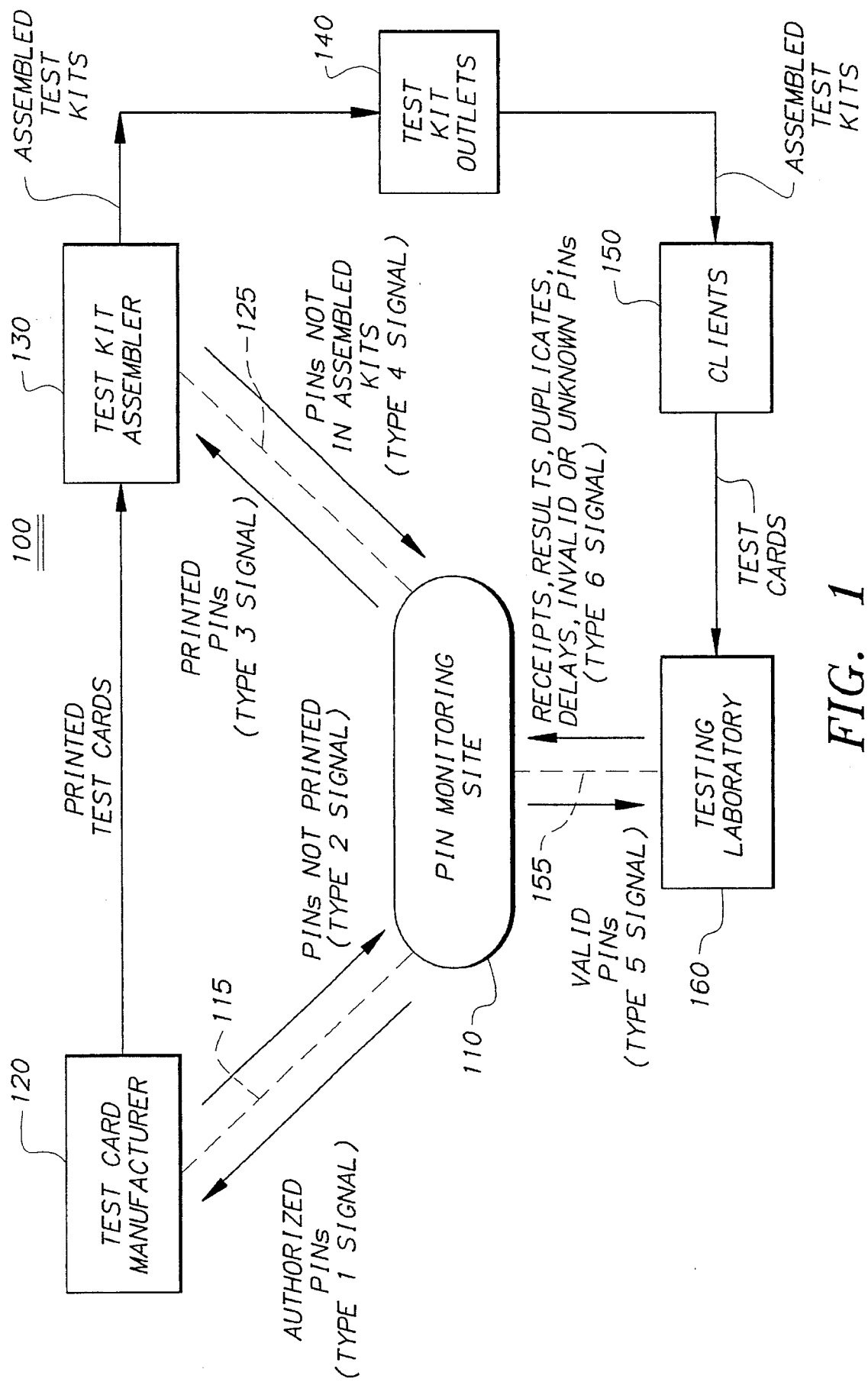
FIG. 1 shows a flow diagram illustrating the operation of a testing system for processing and securely tracking medical test cards in accordance with a preferred embodiment of the present invention.

Referring now to FIG. 1, there is shown a flow diagram illustrating the operation of a testing system 100 for processing and securely tracking medical test cards used in connection with an in-home HIV testing kit according to a preferred embodiment of the present invention. In accordance with the present invention, an individual desiring to use the in-home HIV test kit purchases the kit from a pharmacy or retail outlet. Each test kit includes a single testing card having a unique personal identification number (PIN) printed thereon in both human readable and machine readable (i.e., bar code) format. Status and test result information for all test cards being processed by the testing system 100 is maintained at a central PIN monitoring site 110. The PIN uniquely identifies each test card in the testing system 100 to central monitoring site 110. Significantly, no information relating to the personal identity of an individual using a test card (e.g., name, address, telephone number, social security number) is submitted to or stored at central monitoring site 110 or anywhere else within testing system 100.

In the preferred embodiment of the present invention, test cards for use with the in-home test kits are produced by a test card manufacturer 120 based on a set of PINs provided by PIN monitoring site 110. The test cards manufactured by card manufacturer 120 are then provided to a test kit assembler 130 who combines the manufactured test cards with other materials thereby assembling complete in-home test kits. Next, the assembled test kits are provided to pharmacies and other retail outlets 140 where the kits are purchased by individual clients 150. The individual clients 150 then take the kits home, deposit their blood samples on the test cards, and mail the test cards to a testing laboratory 160. Prior to mailing the test card to the laboratory, each client 160 maintains a copy of the PIN that was affixed to his or her test card. A fixed period of time after the test cards are mailed to the testing laboratory 160, the clients 150 call the central monitoring site 110 to obtain their test results. During these calls, a client caller identifies himself or herself to the central monitoring system 110 only by the PIN number that was affixed to his or her test card.

As the test cards cycle from the manufacturer 120 to the assembler 130, from the assembler 130 to the retail outlets 140, and ultimately from the retail stores 140 to the clients 150 and into the testing lab 160, central monitoring site 110 transmits digital signals to and receives digital signals from manufacturer 120, test kit assembler 130, and testing laboratory 160. By processing these signals, PIN monitoring site 110 is able to maintain current information associated with each active PIN in testing system 100 in a plurality of separate databases. Among other things, for each active PIN, a PIN database at PIN monitoring site 110 stores information representing whether a test card containing the PIN was ever manufactured by manufacturer 120, whether a test kit having a test card with the PIN was ever shipped by assembler 130, whether a test card containing the PIN was received by the test lab 160, the status (e.g., pending or delayed) of any test being performed by test lab 160 on the test card containing the PIN, and a results database at PIN monitoring site 110 stores any test result information (e.g., HIV positive, HIV negative or inconclusive) associated with the test card containing the PIN. In the preferred embodiment, transmission and reception of information amongst PIN monitoring site 110, test card manufacturer 120, test kit assembler 130 and testing laboratory 160 is accomplished via dial-up modem lines 115 and 125, and dedicated modem line 155. Modem lines 115, 125 and 155 are preferably coupled to a general purpose computer system at PIN monitoring site 110. In addition, modem lines 115, 125 and 155 are preferably coupled to separate stand-alone personal computing systems respectively located at manufacturer 120, test kit assembler 130 and testing lab 160.

Figure 2:
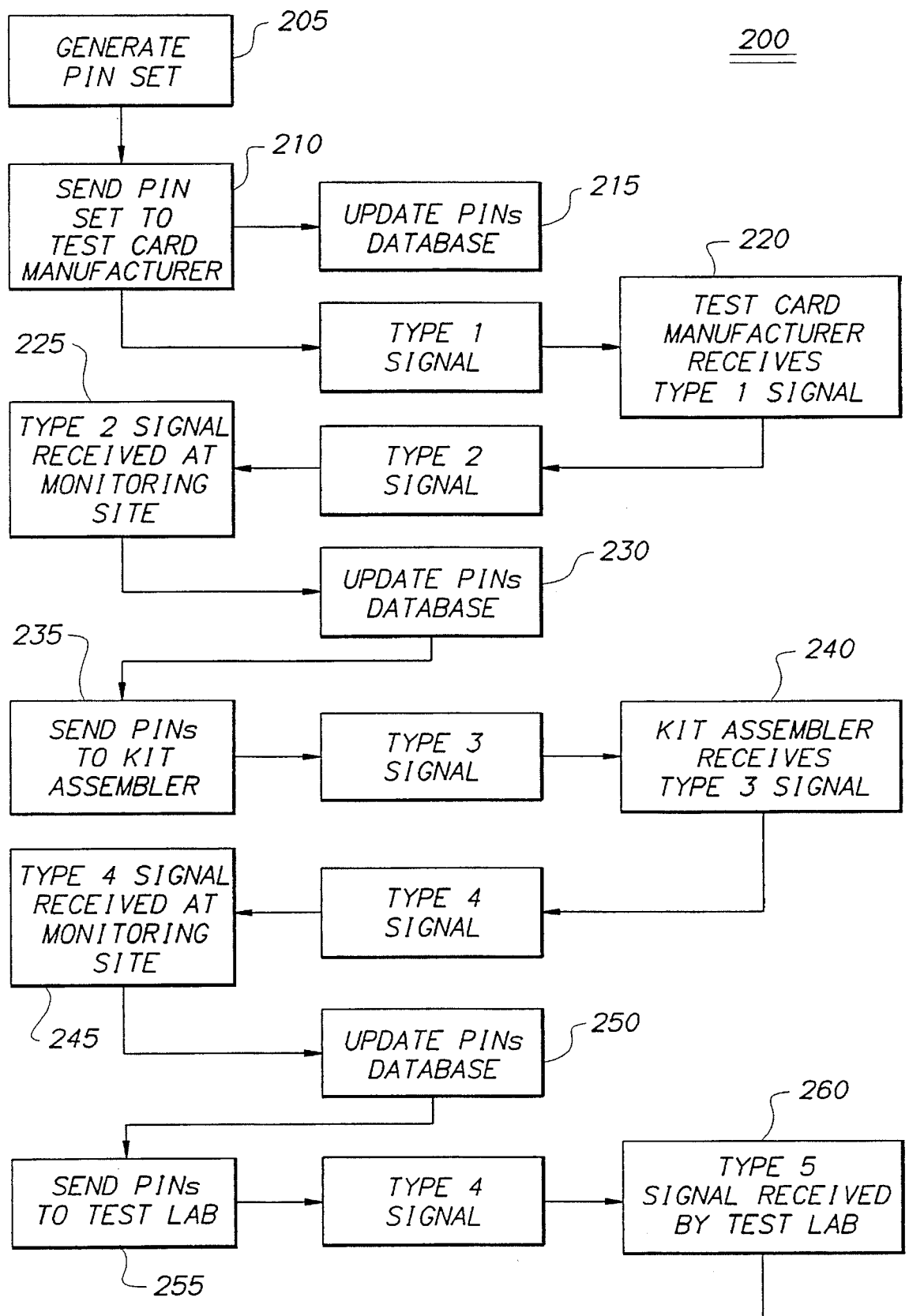
FIGS. 2 and 2A show a further flow diagram illustrating the operation of a system for securely tracking medical test cards in accordance with a preferred embodiment of the present invention.
Figure 2A:
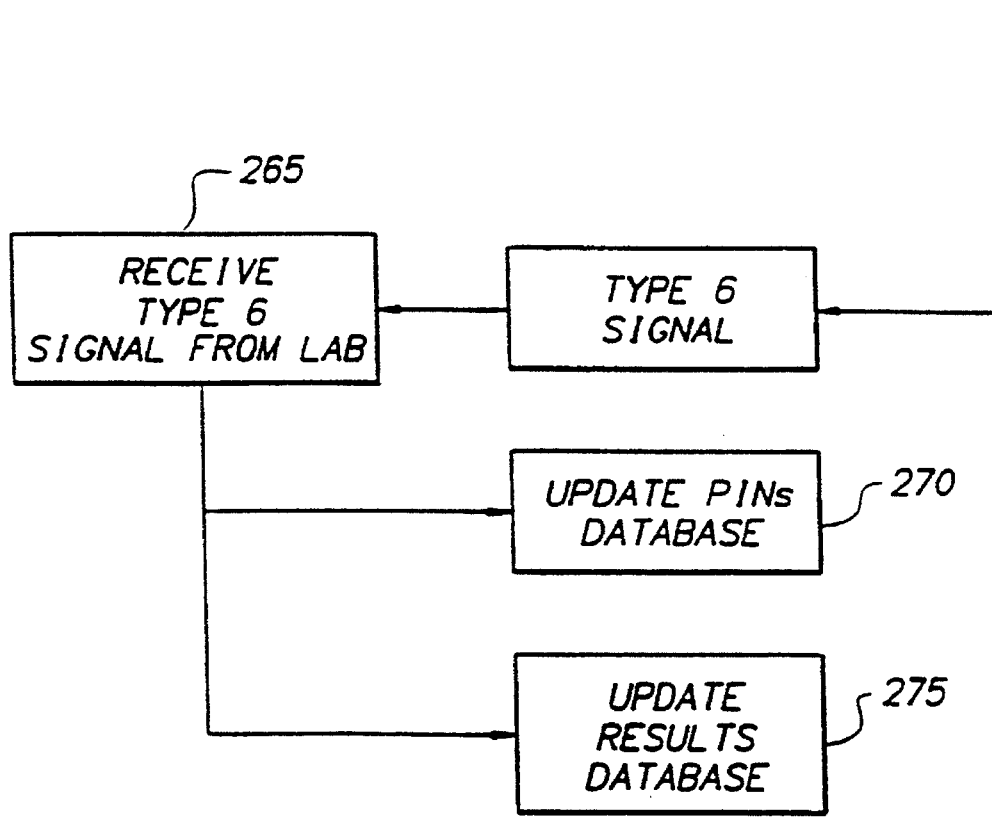

Referring now to FIGS. 2 and 2A, there is shown a further flow diagram illustrating the operation of a system 200 for securely tracking medical test cards in accordance with a preferred embodiment of the present invention. Initially, at step 205, the central PIN monitoring site 110 generates a first set of unique PINs for use in testing system 100. In a preferred embodiment, each PIN in the set is a unique 14-digit number. A common 5-digit job number is then appended to each PIN in the set. In step 210, a Type 1 digital signal representative of the first set of PINs with the common 5-digit job number appended thereto is transmitted via dial-up modem line 115 from PIN monitoring site 110 to test card manufacturer 120. Alternatively, the Type 1 signal is transmitted from PIN monitoring site 110 to test card manufacturer 120 by diskette. In step 215, central PIN monitoring site 110 initially updates its PIN database by storing the first set of unique PINs having the 5-digit job number on the PIN database and designating each such PIN as AUTHORIZED. PINs bearing the AUTHORIZED designation represent test cards that have been authorized for manufacture.

In step 220, the test card manufacturer 120 receives a Type 1 digital signal transmitted by PIN monitoring system 110, and then attempts to produce test cards corresponding to all the PINs transmitted. As explained later in connection with FIG. 3, each test card produced by test card manufacturer 120 will bear its associated 14-digit PIN in both human readable and bar code format. As a result of manufacturing shrinkage and test cards that are pulled by manufacturer 120 for quality control purposes, manufacturer 120 will typically not produce for shipment a test card corresponding to every single PIN generated in step 205. However, after the test card manufacturer 120 has completed production of test cards for the PINs transmitted from PIN monitoring site 110 in step 210, the test card manufacturer 120 will transmit a Type 2 digital signal via dial-up modem line 115 back to PIN monitoring site 110. This Type 2 digital signal will represent the PINs corresponding to those test cards that were not actually manufactured for shipment either as a result of manufacturing shrinkage or because such cards were pulled for quality control purposes. Alternatively, the Type 2 signal may be transmitted from test card manufacturer 120 to PIN monitoring site 110 by diskette. Upon receipt of a Type 2 digital signal in step 225, the PIN monitoring site 110 will update its PIN database (in step 230) by designating as INVALID each PIN for which no test card was produced for shipment. In addition, in step 230, the PIN monitoring site 110 will designate as MANUFACTURED each PIN for which a test card was produced for shipment by manufacturer 120.

In step 235, the PIN monitoring site 110 transmits a Type 3 digital signal to the test kit assembler 130. The Type 3 signal is representative of the PINs corresponding to the test cards actually produced for shipment by test card manufacturer 120. When the Type 3 signal is transmitted to test kit assembler 130, PIN monitoring site 110 designates as ASSEMBLER (which stands for "at assembler") each PIN represented by the Type 3 signal. The third digital signal is transmitted via dial-up modem line 125 from PIN monitoring site 110 to test kit assembler 130. Alternatively, the Type 3 files may be transmitted from PIN monitoring site 110 to test card assembler 130 via diskette. The PINs transmitted to the test kit assembler in step 235 will continue to bear the same 5-digit job number originally assigned to such PINs in step 205. When the Type 3 digital signal is transmitted to the test kit assembler 130, the test cards manufactured by test card manufacturer 120 are shipped from test card manufacturer 120 to test kit assembler 130. Each pallet of test cards shipped from the test card manufacturer 120 to the test kit assembler 130 preferably has affixed thereto the common 5-digit job number originally assigned to the first set of PINs during step 205.

Upon receipt of the test cards and the Type 3 digital signal in step 240, the test kit assembler 130 begins assembling test kit packages. Each test kit package will contain one of the test cards provided by the test card manufacturer 120, as well as other materials including pamphlets on the HIV virus and AIDs, and a mailer for shipping the test card to the testing lab 160. The test kit assembler 130 assigns a common lot number to all the kits assembled. As a result of manufacturing shrinkage and test kits that are pulled by assembler 130 for quality control testing purposes, assembler 130 will typically not produce for shipment a test kit corresponding to every single PIN provided to assembler 130 in the Type 3 digital signal. However, after the test kit assembler 130 has completed production of test kits corresponding to the PINs transmitted from PIN monitoring site 110 in step 235, the test kit assembler 130 will transmit a Type 4 digital signal via dial-up modem line 125 back to PIN monitoring site 110. A Type 4 digital signal will represent the PINs corresponding to those test kits that were not actually assembled for shipment. Alternatively, the Type 4 signals may be transmitted from test kit assembler 130 to PIN monitoring site 110 by diskette. Upon receipt of a Type 4 digital signal in step 245, the PIN monitoring site 110 will update its PIN database (in step 250) by designating as INVALID each PIN for which no test kit was assembled for shipment. In step 250, PIN monitoring site 110 will also update its PIN database by designating as RELEASED each PIN for which a test kit was assembled for shipment. Following transmission of a Type 4 digital signal from the test kit manufacturer 130 to the PIN monitoring site 110, test kit manufacturer 130 ships its assembled test kits to retail outlets 140 where the test kits are purchased by clients 150.

In step 255, the PIN monitoring site 110 transmits (via dedicated modem line 155) a Type 5 digital signal to the test lab 150 representative of the PINs corresponding to the test kits actually assembled for shipment and released to retail outlets 140 by test kit assembler 130, thereby alerting test lab 160 of the PINs corresponding to the test cards that test lab 160 should expect to receive from clients 150. The PINs transmitted to the test lab in step 255 will continue to bear the same 5-digit job number originally assigned to such PINs in step 205. In step 260, testing lab 160 receives a Type 5 digital signal and stores in a testing laboratory PIN database (located at laboratory 160) the PINs corresponding to the test kits actually assembled for shipment and released to retail outlets 140 by test kit assembler 130. Each PIN stored in the testing laboratory PIN database in step 260 is initially designated as VALID.

As the test lab 160 receives test cards from clients 150, test lab 160 compares the PIN of each received test card to the list of PINs stored in step 260. If the PIN of a received card corresponds to a VALID PIN stored in the testing laboratory PIN database, the PIN is designated as RECEIVED by the testing lab 160 and formal testing is then begun to determine whether the blood on the test card represents an HIV positive or HIV negative result. Approximately one to three days later, after the test lab has tested the test card, result information (HIV positive, HIV negative, test inconclusive) corresponding to the PIN is also stored by test lab 160. Alternatively, if the PIN on a test card received at the lab corresponds to a PIN that is either designated as INVALID in the testing laboratory database or which is not listed (i.e., UNKNOWN) to the testing laboratory database, the test card is not processed for testing. In addition, if the PIN on a test card received by the testing laboratory 160 corresponds to a PIN that was previously designated as received, the test card is flagged as a duplicate and the PIN associated with the test card is designated as INVALID in the testing laboratory PIN database. Thus, in the event that counterfeit test cards are produced by an unauthorized third party, it is unlikely that consumers attempting to use such unauthorized test cards could obtain any test result information, because the unauthorized test cards would not be likely to contain valid or non-duplicative PINs and, as such, would not be accepted for processing by test lab 160.

In the preferred embodiment of the present invention, test lab 160 and PIN monitoring site 110 are coupled by dedicated modem line 155 and, on a regular basis, test lab 160 transmits a Type 6 digital signal to PIN monitoring site 110. Each Type 6 signal sent will transmit to PIN monitoring site 110 PINs designated as RECEIVED by test lab 160, a list of all INVALID, UNKNOWN or duplicative PINs which test lab 160 received but did not process, and any available test result information corresponding to PINs on the test cards being processed by test lab 160. PIN monitoring site 110 preferably receives the transmission of Type 6 signals from test lab 160 (step 265) on an hourly basis. Upon receipt of this transmission, PIN monitoring site 110 updates its PIN database (in step 270) by designating each VALID PIN received by the test lab as RECEIVED and by designating each duplicative PIN received by testing laboratory 160 as INVALID. In addition, in step 275, the test results database at PIN monitoring site 110 is updated with any test result information provided in the Type 6 signal for PINS corresponding to test cards previously received by the test lab.

In a further aspect of the present invention, a Type VII signal (not shown in FIGS. 2 and 2A) is periodically transmitted from PIN monitoring site 110 to testing laboratory 160. The Type VII signal is representative of PINS that were previously provided to testing laboratory 160 by monitoring site 110 (in step 260), but which have since become INVALID. PINs initially designated as RELEASED by monitoring site 110 will be rendered INVALID if monitoring site 110 determines that the test kit associated with the PIN is either defective or has reached its expiration date. Thus, monitoring site 110 uses Type VII signals to periodically alert testing laboratory 160 of PINs that have become invalid subsequent to the time they were released to outlets 140. Upon receipt of a Type VII signal, testing laboratory 160 updates its testing laboratory database by designating as INVALID each PIN represented by the type VII signal.

By communicating with test card manufacturer 120, test kit assembler 130 and test lab 160 as test cards are generated and cycle through testing system 100, monitoring site 100 is able to accurately track both location information and status information for each test card in the system on a current basis.

Figure 3:
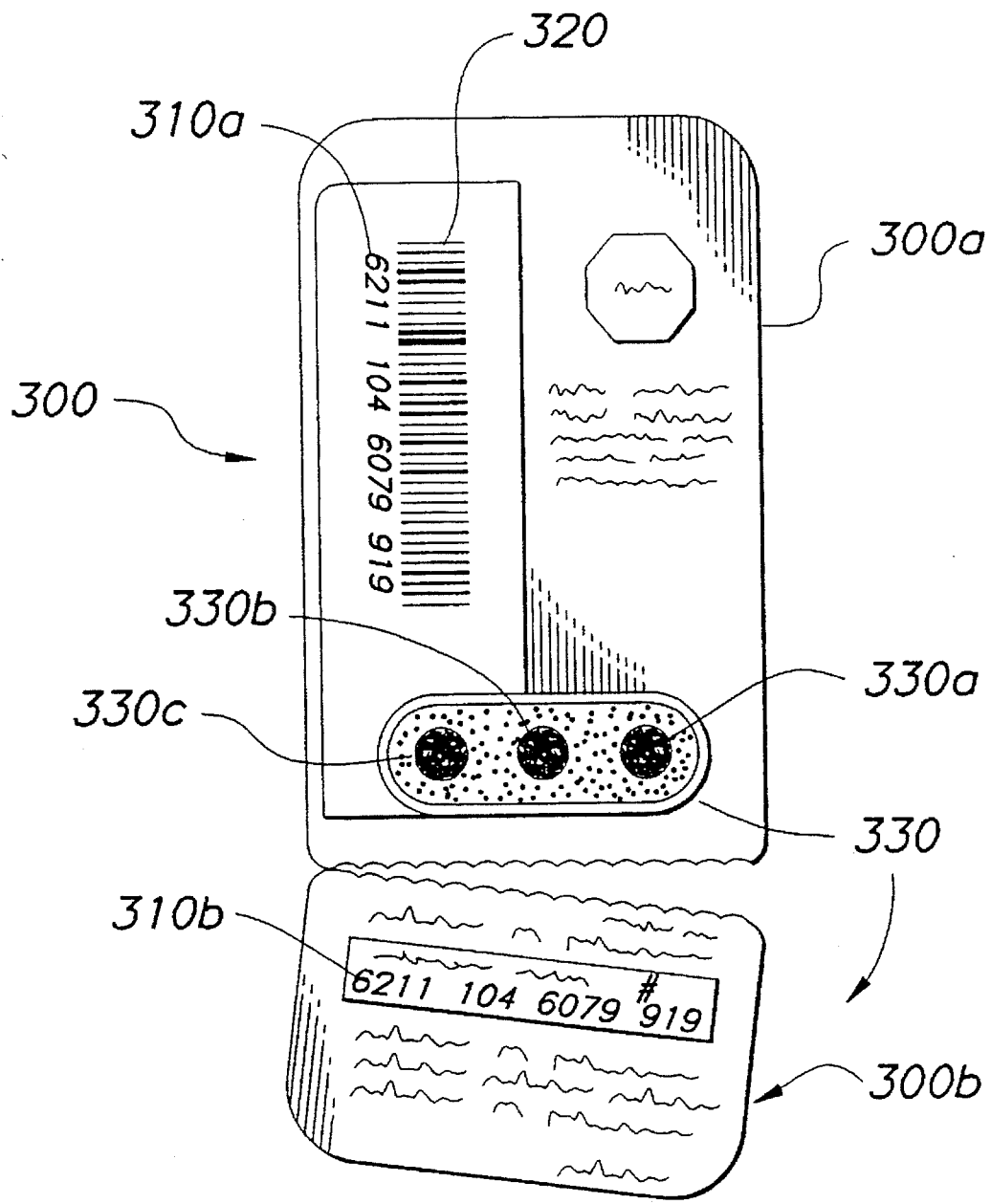
FIG. 3 shows an exemplary test card for use in conjunction with the preferred embodiment of the present invention.

Referring now to FIG. 3, there is shown a preferred embodiment of test card 300 for use in conjunction with the present invention. Test card 300 is intended to be used as a simple means for a client 150 to apply his or her blood sample to the card (in zones 330a, 330b, 330c), detach the identification portion (300b) of the card, and return the test portion (300a) of the card to testing laboratory 160 for evaluation. Card 300 is preferably rectangular in shape and contains a perforation which facilitates the separation of test portion 300a from identification portion 300b by a client 150. Each test card 300 has a unique PIN 310a, 310b (generated in step 205) printed both on the test portion 300a and identification portion 300b of the card. In addition, in order to allow manufacturer 120, assembler 130 and test lab 160 to more easily identify the cards as they pass through their respective facilities, a bar code representation 320 of PIN 310a, 310b is also printed on test portion 300b.

The present invention may be embodied in other specific forms without departing from the spirit or essential attributes of the invention. Accordingly, reference should be made to the appended claims, rather than the foregoing specification, as indicating the scope of the invention.

What is claimed is:

1. A method for tracking with a central monitoring system status and result information associated with a plurality of test cards, each of said test cards being anonymously associated with a patient such that said patient's identity is unknown to said central monitoring system, said central monitoring system being formed of a personal identification number database and a test results database, comprising the steps of:

(A) storing a first set of unique personal identification numbers (PINs) on said personal identification number database;

(B) providing a first digital signal representative of PINs from said first set of unique PINs to a test kit assembler;

(C) receiving in said central monitoring system a second digital signal from said test kit assembler representative of test kits actually assembled, each of said test kits actually assembled including a test card having one of said unique PINs from said first set of unique PINs associated therewith, and tracking said first set of unique PINs by updating said personal identification number database in response to said second digital signal;

(D) providing, from said central monitoring system, a third digital signal representative of a second set of unique PINs to a test lab in response to said second digital signal; and (E) receiving in said central monitoring system a fourth digital signal from said test lab representative of test cards received at said test lab from patients, and tracking said first set of unique PINs by updating said personal identification number database and said test results database in response to said fourth digital signal;

wherein each of said test cards received at said test lab is known to said central monitoring system only by one of said unique PINs from said first set of unique PINs, and wherein an identity of a patient associated with each of said test cards received at said test lab is anonymous to said central monitoring system.

2. The method of claim 1, further comprising the steps of:

(F) providing, from said central monitoring system, a fifth digital signal representative of said first set of unique PINs to a test card manufacturer;

(G) receiving in said central monitoring system a sixth digital signal from said test card manufacturer representative of test cards actually manufactured, each of said test cards actually manufactured having one of said unique PINs from said first set of unique PINS associated therewith, and tracking said first set of unique PINs by updating said personal identification number database in response to said sixth digital signal; and wherein said third digital signal representative of said second set of unique PINs is provided to said test lab in step (D) in response to said second digital signal and said sixth digital signal.

3. The method of claim 2, wherein said second set of unique PINs is a subset of said first set of unique PINs representing PINs associated with test kits assembled by said test kit assembler and shipped to test kit outlets.

4. The method of claim 3, wherein said first digital signal in step (B) is provided to said test kit assembler from said central monitoring system via a first dial-up modem link, and wherein said second digital signal is received in said central monitoring system from said test kit assembler via said first dial-up modem link.

5. The method of claim 4, wherein said fifth digital signal in step (F) is provided to said test card manufacturer from said central monitoring system via a second dial-up modem link, and wherein said sixth digital signal is received in said central monitoring system from said test card manufacturer via said second dial-up modem link.

6. The method of claim 5, wherein said third digital signal in step (D) is provided to said test lab from said central monitoring system via a dedicated modem line, and wherein said fourth digital signal is received in said central monitoring system from said test lab via said dedicated modem line.

7. The method of claim 6, wherein said fourth digital signal is further representative of test cards received at said test lab having duplicative PINs associated therewith.

8. The method of claim 7, wherein said fourth digital signal is further representative of test result and test status information associated with each valid test card received at said test lab.

9. An apparatus for tracking with a central monitoring system status and result information associated with a plurality of test cards, each of said test cards being anonymously associated with a patient such that said patient's identity is unknown to said central monitoring system, said central monitoring system being formed of a personal identification number database and a test results database, comprising:

(A) means for storing a first set of unique personal identification numbers (PINs) on said personal identification number database;

(B) means for providing a first digital signal representative of PINS from said first set of unique PINs to a test kit assembler;

(C) means for receiving in said central monitoring system a second digital signal from said test kit assembler representative of test kits actually assembled, each of said test kits actually assembled including a test card having one of said first set of unique PINs associated therewith, and means for tracking said first set of unique PINs by updating said personal identification number database in response to said second digital signal;

(D) means for providing, from said central monitoring system, a third digital signal representative of a second set of unique PINs to a test lab in response to said second digital signal; and (E) means for receiving in said central monitoring system a fourth digital signal from said test lab representative of test cards received at said test lab from patients, and means for tracking said first set of unique PINs by updating said personal identification number database and said test results database in response to said fourth digital signal;

wherein each of said test cards received at said test lab is known to said central monitoring system only by one of said unique PINs from said first set of unique PINs, and wherein an identity of a patient associated with each of said test cards received at said test lab is anonymous to said central monitoring system.

10. The apparatus of claim 9, further comprising:

(F) means for providing, from said central monitoring system, a fifth digital signal representative of said first set of unique PINs to a test card manufacturer;

(G) means for receiving in said central monitoring system a sixth digital signal from said test card manufacturer representative of test cards actually manufactured, each of said test cards actually manufactured having one of said unique PINs from said first set of unique PINs associated therewith, and means for tracking said first set of unique PINs by updating said personal identification number database in response to said sixth digital signal; and wherein said third digital signal representative of said second set of unique PINs is provided to said test lab in response to said second digital signal and said sixth digital signal.

11. The apparatus of claim 10, wherein said second set of unique PINs is a subset of said first set of unique PINs representing PINs associated with test kits assembled by said test kit assembler and shipped to test kit outlets.

12. The apparatus of claim 11, wherein said means for providing said first digital signal comprises a first dial-up modem link, and wherein said means for receiving said second digital signal is also comprised of said first dial-up modem link.

13. The apparatus of claim 12, wherein said means for providing said fifth digital signal comprises a second dial-up link modem, and wherein said means for receiving said sixth digital signal is also comprised of said second dial-up modem link.

14. The apparatus of claim 13, wherein said means for providing said third digital signal comprises a dedicated modem line, and wherein said means for receiving said fourth digital signal is also comprised of said dedicated modem line.

15. The apparatus of claim 14, wherein said fourth digital signal is further representative of test cards received at said test lab having duplicative PINs associated therewith.

16. The apparatus of claim 15, wherein said fourth digital signal is further representative of test result and test status information associated with each valid test card received at said test lab.

* * * * *